United States Patent
Ito et al.

(10) Patent No.: US 7,495,751 B2
(45) Date of Patent: Feb. 24, 2009

(54) MEASURING APPARATUS

(75) Inventors: Yuki Ito, Kyoto (JP); Hitoshi Hata, Kyoto (JP); Hiroyuki Nakanishi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 61 days.

(21) Appl. No.: 11/664,206

(22) PCT Filed: Sep. 28, 2005

(86) PCT No.: PCT/JP2005/017889

§ 371 (c)(1),
(2), (4) Date: Mar. 29, 2007

(87) PCT Pub. No.: WO2006/035839

PCT Pub. Date: Apr. 6, 2006

(65) Prior Publication Data

US 2007/0291253 A1    Dec. 20, 2007

(30) Foreign Application Priority Data

Sep. 30, 2004    (JP) .............................. 2004-287306

(51) Int. Cl.
*G01N 33/48* (2006.01)
(52) U.S. Cl. .......................................... 356/39; 356/40
(58) Field of Classification Search ........................ None
See application file for complete search history.

(56) References Cited

U.S. PATENT DOCUMENTS 6,121,050 A    9/2000    Han

2005/0036146 A1 *    2/2005    Braig et al. .................. 356/436

FOREIGN PATENT DOCUMENTS

| JP | 4-151546 | 5/1992 |
| JP | 2001-091518 | 4/2001 |

* cited by examiner

*Primary Examiner*—Michael P Stafira
(74) *Attorney, Agent, or Firm*—Hamre, Schumann, Mueller & Larson, P.C.

(57) ABSTRACT

A measuring apparatus is provided with a light source (4), a first light-receiving element (5) and a second light-receiving element (6) which output signals corresponding to light intensity, a calculating part (12) and a memory part (13). The first light-receiving element (6) and the light source (4) are arranged so that transmitted light emitted from the light source and passed through a sample is received by the first light-receiving element (5). The second light-receiving element (6) is arranged so as to receive light other than the transmitted light emitted from the light source (4). In the memory part (13), a correlation between the output value of the first light-receiving element (5) and the output value of the second light-receiving element (6) when light is emitted from the light source (4) in a state where the sample is not present is stored. The calculating part calculates absorbance of a target component contained in the sample, from the output values of the first light-receiving element (5) and the second light-receiving element (6) when light is emitted from the light resource (4) in the state where the sample present, and from the correlation.

6 Claims, 11 Drawing Sheets

MEASURING APPARATUS

TECHNICAL FIELD

The present invention relates to a measuring apparatus. Particularly, the present invention relates to an absorbance measuring apparatus for measuring the absorbance of a target component contained in a sample.

BACKGROUND ART

Currently, absorbance measurement methods are applied to analyses of various components. Component analysis by such an absorbance measurement method is carried out in accordance with the following procedures, for example. First, a transparent container (cell) containing a specimen mixed with a pigment is irradiated with light having a wavelength corresponding to the pigment, from a light source such as a halogen lamp or LED. Next, the intensity I of the transmitted light that has passed through the transparent container and the specimen is measured with a light-receiving element.

Later, the absorbance ($=\log_{10}(I_0/I)$) is calculated from the measured intensity I of the transmitted light and a blank value $I_0$ that has been measured in advance. Thereby, the component amount of the material labeled by a pigment can be detected (see Patent Document 1, for example). The blank value $I_0$ is measured by irradiating a water-containing or empty cell with light from the light source. The absorbance measurement method is not limited to the above-mentioned transmission type utilizing transmitted light, but a reflection type using light reflected by a measurement target is known as well.

The absorbance measurement method is used also for measuring a blood glucose level in a blood. A blood glucose meter for measuring a blood glucose level by the absorbance measurement method is called generally a colorimetric blood glucose meter. For decreasing the size, a colorimetric blood glucose meter developed to be carried by a patient includes not a transparent container but a disposable sensor or chip made of a nonwoven fabric or the like.

The sensor or chip is impregnated with a reagent that develops color as a result of a reaction with glucose in the blood. Since the transmitted light quantity of light passed through the sensor or chip varies depending on the color development level, the blood glucose level can be obtained from the measured absorbance. In such a portable colorimetric blood glucose meter, measurement of the blank value is carried out without attaching a sensor or a chip.

Patent document 1: JP 2001-91518 A

DISCLOSURE OF INVENTION

Problem to be Solved by the Invention

However, since the light quantity of a halogen lamp, LED or the like as the light source varies over time, the light quantity of the transmitted light and reflected light will vary accordingly. Therefore, for obtaining an accurate absorbance in a conventional absorbance measurement method, changes in the light quantity of the light source over time must be taken into consideration. Since a blank value must be measured prior to a measurement of the absorbance in a conventional absorbance measuring apparatus (blood glucose meter), complicated operations are required before starting an actual measurement. Moreover, quite a long preparation time is required for starting the measurement.

Moreover, particularly for a small blood glucose meter that employs a transmission type absorbance measurement method, the sensor or chip as a measurement target is inserted into an insertion hole formed in the blood glucose meter. Therefore, the blank value cannot be measured after inserting the sensor or chip.

It is considered that complication in the operations can be reduced by providing the blood glucose meter with an optical system for only measurement of the blank value. In this case, an optical element provided to the optical system for only the measurement of the blank value is used for an actual measurement as well as the measurement of the blank value, thereby improving the accuracy in measurement of the absorbance.

In this case, however, the number of parts will increase and the apparatus structure will be complicated, thereby causing problems such as an increase in size of the apparatus and also increase in the cost. Moreover, since there are some differences in general between the optical system only for the measurement of the blank value and the optical system for an actual measurement, an accurate absorbance cannot be obtained without correcting the differences.

Therefore, with the foregoing in mind, it is an object of the present invention to provide a measuring apparatus solving the above-mentioned problems, having excellent operability, and capable of performing an accurate measurement of absorbance.

Means for Solving Problem

In order to achieve the above object, a measuring apparatus according to the present invention is an apparatus for measuring an absorbance of a target component contained in a sample; and the measuring apparatus includes a light source for emitting light having a wavelength to be absorbed by the target component, a first light-receiving element and a second light-receiving element for outputting signals corresponding to the intensity of the received light, a calculating part and a memory part, wherein the first light-receiving element and the light source are arranged so that the transmitted light emitted from the light source and passed through the sample is received by the first light-receiving element, the second light-receiving element is arranged to receive light other than the transmitted light emitted from the light source, the memory part stores a correlation between the output value of the first light-receiving element and the output value of the second light-receiving element when light is emitted from the light source in a state where the sample is not present, and the calculating part calculates the absorbance of the target component from the output values of the first light-receiving element and the second light-receiving element when light is emitted from the light source in a state where the sample is present, and from the correlation.

Effects of the Invention

Due to the above-mentioned features, in a measuring apparatus according to the present invention, since there is no need for preliminary measurement of the blank value before a measurement of the absorbance, the measuring apparatus of the present invention has excellent operability. Moreover, the absorbance measured with the measuring apparatus of the present invention provides accurate values including the changes over time in the light quantity of the light source.

DESCRIPTION OF THE INVENTION

Figure 1:
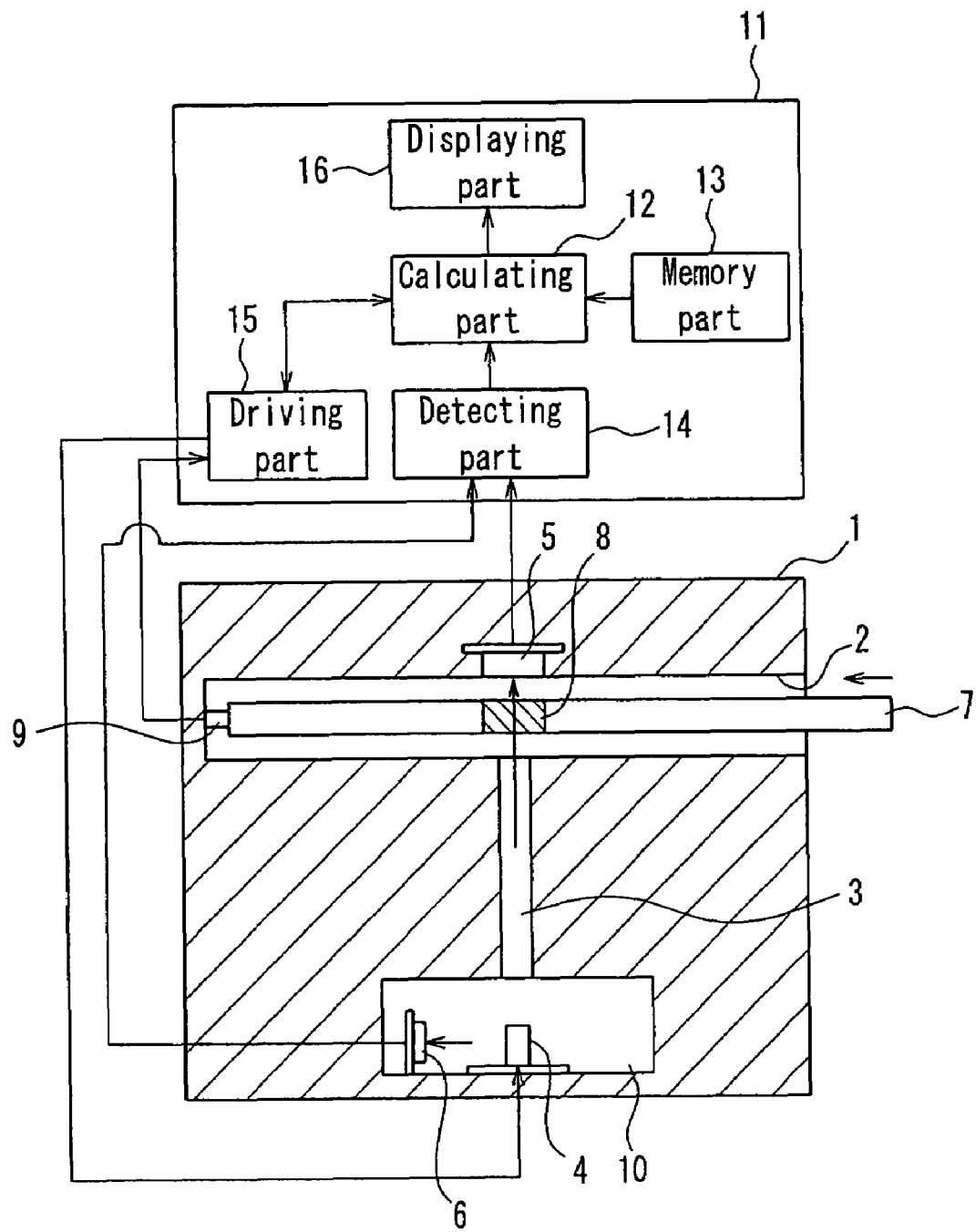
FIG. 1 is a schematic view showing a schematic configuration of a measuring apparatus according to Example 1 of the present invention.

A measuring apparatus according to the present invention is a measuring apparatus for measuring an absorbance of a target component contained in a sample, the measuring apparatus including: a light source for emitting light having a wavelength to be absorbed by the target component, a first light-receiving element and a second light-receiving element for outputting signals corresponding to the intensity of received light, a calculating part, and a memory part. The first light-receiving element and the light source are arranged so that transmitted light emitted from the light source and passed through the sample is received by the first light-receiving element, the second light-receiving element is arranged to receive light other than the transmitted light emitted from the light source, the memory part stores a correlation between an output value of the first light-receiving element and an output value of the second light-receiving element when light is emitted from the light source in a state where the sample is not present, and the calculating part calculates the absorbance of the target component from the output values of the first light-receiving element and the second light-receiving element when light is emitted from the light source in a state where the sample is present, and from the correlation.

In a first embodiment of the above-described measuring apparatus according to the present invention, the correlation is expressed as a proportionality constant $t_1$ calculated by substituting in Formula (1) below an output value $A_{10}$ of the first light-receiving element and an output value $B_{10}$ of the second light-receiving element when light is emitted from the light source in a state where the sample is not present; the calculating part calculates S on the basis of Formula (2) below, where $A_1$ and $B_1$ denote respectively the output values of the first light-receiving element and the second light-receiving element when light is emitted from the light source in a state where the sample is present, and S denotes the absorbance of the target component. According to the first embodiment, an accurate absorbance can be calculated in a simple manner.

[Equation 5]
$$t_1 = A_{10}/B_{10} \quad (1)$$

[Equation 6]
$$S = \left(-\log\frac{A_1}{B_1 \cdot t_1}\right) \quad (2)$$

It is also possible in the first embodiment that when the sample is not present, the calculating part allows the light source to emit light so as to acquire the output value $A_{10}$ of the first light-receiving element and the output value $B_{10}$ of the second light-receiving element, substitutes in the above Formula (1) the acquired output value $A_{10}$ of the first light-receiving element and the output value $B_{10}$ of the second light-receiving element so as to calculate the proportionality constant $t_1$, stores the calculated proportionality constant $t_1$ in the memory part, and calculates the absorbance S of the target component by using the stored proportionality constant $t_1$.

In a second embodiment for the above-mentioned measuring apparatus according to the present invention, the sample contains a component to hinder an advance of light entering the sample; the measuring apparatus further includes a second light source for emitting light having a wavelength not to be absorbed by the target component. The second light source is arranged so that second transmitted light emitted from the second light source and passed through the sample is received by the first light-receiving element, and that light other than the second transmitted light emitted from the second light source is received by the second light-receiving element, the memory part further stores a correlation between an output value $A_{20}$ of the first light-receiving element and an output value $B_{20}$ of the second light-receiving element when light is emitted from the second light source in a state where the sample is not present. The correlation between the output value $A_{20}$ of the first light-receiving element and the output value $B_{20}$ of the second light-receiving element is expressed as a proportionality constant $t_2$ that is calculated by substituting in Formula (3) below the output value $A_{20}$ of the first light-receiving element and the output value $B_{20}$ of the second light-receiving element, and the calculating part calculates the absorbance S of the target component on the basis of Formula (4) below by using the output value $A_2$ of the first light-receiving element and the output value $B_2$ of the second light-receiving element when light is emitted from the second light source in a state where the sample is present, and further the correlation between the output value $A_{20}$ of the first light-receiving element and the output value $B_{20}$ of the second light-receiving element. According to the second embodiment, even when the sample contains a component that is other than the target component and that hinders transmission of light from the light source, the absorbance of the target component can be measured accurately.

[Equation 7]
$$t_2 = A_{20}/B_{20} \quad (3)$$

[Equation 8]
$$S = \left(-\log\frac{A_1}{B_1 \cdot t_1}\right) - \left(-\log\frac{A_2}{B_2 \cdot t_2}\right) \quad (4)$$

It is also possible in the second embodiment that when the sample is not present, the calculating part allows the second light source to emit light so as to acquire the output value $A_{20}$ of the first light-receiving element and the output value $B_{20}$ of the second light-receiving element, substitutes in the above Formula (3) the acquired output value $A_{20}$ of the first light-receiving element and the output value $B_{20}$ of the second light-receiving element so as to calculate the proportionality constant $t_2$, stores the calculated proportionality constant $t_2$ in the memory part, and calculates the absorbance S of the target component by using the stored proportionality constant $t_2$.

In the measuring apparatus according to the present invention, the target component can be glucose that is contained in the sample and develops color due to a reagent. Particularly in the second embodiment, for example, an accurate absorbance can be measured even when the sample is a blood that contains blood cell components, and the target component is glucose that is contained in the blood and develops color due to a reagent.

EXAMPLE 1

Hereinafter, a measuring apparatus according to Example 1 of the present invention will be described with reference to the attached FIGS. 1 to 6. First, the configuration of the measuring apparatus according to Example 1 will be described with reference to FIG. 1. FIG. 1 is a schematic view showing a schematic configuration of the measuring apparatus according to Example 1 of the present invention.

In Example 1, the measuring apparatus is employed as a calorimetric blood glucose meter. The sample is a blood plasma component obtained by centrifuging a patient's blood. The target component to be measured is glucose that is contained in the sample and develops color due to a reagent. Specifically, as shown in FIG. 1, the sample is subjected to a measurement in a state of being impregnated in a reagent part 8 of a sensor 7.

The sensor 7 is obtained by using as a base a resin such as a polyethylene resin, a polyethylene terephthalate (PET) resin, a polystyrene resin and a polyvinyl chloride resin, which is shaped into a strip. The sensor 7 can be a monolayer or a multilayer formed by laminating a plurality of strip-shaped bases. When the sensor 7 is formed as a multilayer, for example, it is preferable that a slit (not shown) is formed in a base as an intermediate layer, and that the slit is used as a channel to introduce the sample into the reagent part. In such a case, it is preferable that an open hole is formed in a base as an upper layer to be communicated with the slit in the intermediate layer and that this open hole is used as an inlet for the sample.

The reagent part 8 is impregnated with a reagent that develops color due to a reaction with glucose, for example, glucoseoxidase, peroxidase, 4-aminoantipyrine, N-ethyl-N-(2-hydroxy-3-sulfopropyl)-m-toluidine.sodium, and the like. Therefore, when a sample is dripped on the reagent part 8, a color corresponding to the concentration of glucose contained in the sample will be developed.

As shown in FIG. 1, the measuring apparatus according to the Example 1 includes an optical unit 1 and a calculation unit 11. The optical unit 1 includes a light source 4 for irradiating the sample with light, a first light-receiving element 5 for receiving transmitted light passed through the sample, and a second light-receiving element 6 for receiving light other than the transmitted light emitted from the light source.

In Example 1, both the first light-receiving element 5 and the second light-receiving element 6 are photodiodes for outputting signals corresponding to the intensity of received light. Alternatively, photo-transistors, CCD, CMOS or the like can be used for the first light-receiving element 5 and the second light-receiving element 6.

In Example 1, the light source 4 is a light-emitting diode. Alternatively, a halogen lamp, a semiconductor laser or the like can be used for the light source 4. The wavelength of the light emitted from the light source 4 is set so that the emitted light will be absorbed by the target component that has developed color due to a reaction with the reagent.

Moreover, in Example 1, the optical unit 1 includes also an insertion hole 2 for inserting the sensor 7, an optical path 3, and a light source chamber 10 for containing the light source 4. The optical path 3 can be formed of a transparent resin material or glass, or it can be a simple hollow. The optical path 3 is arranged to be perpendicular to the sensor 7, with one end portion is exposed toward the sidewall of the insertion hole 2 while the other end portion is exposed toward the ceiling plane of the light source chamber 10. The reagent part 8 of the sensor 7 is arranged to face the one end portion of the optical path 3 when the sensor 7 is inserted deeply into the insertion hole 2.

In FIG. 1, the hatched area denotes a shielded portion. In FIG. 1, numeral 9 denotes a limit switch for detecting that the sensor 7 is inserted into the insertion hole 2.

The first light-receiving element 5 is arranged so as to expose its light-receiving plane toward the sidewall of the insertion hole 2 on the extension line of the optical path 3. Therefore, transmitted light emitted from the light source 4 and passed through the sample is received by the first light-receiving element 5.

The second light-receiving element 6 is arranged in the light source chamber 10, with its light-receiving plane facing the light source 4. Therefore, the second light-receiving element 6 receives light other than the transmitted light emitted from the light source 4, that is, light emitted from the light source 4 but not passed through the sensor 7. The arrangement of the second light-receiving element 6 is not limited to the arrangement as shown in FIG. 1, but for example, the second light-receiving element 6 can be arranged in a package of the light-emitting diode constituting the light source 4.

The calculation unit 11 includes a calculating part 12, a memory part 13, a detecting part 14, a driving part 15 and a displaying part 16. The driving part 15 serves for detection of the sensor 7 and allows the light source 4 to emit light. More specifically, the driving part 15 is connected to the limit switch 9. When the limit switch 9 is turned on (when the sensor 7 is inserted into the insertion hole 2), the driving part 15 outputs a signal for the notification (notification signal) to the calculating part 12. When the notification signal is outputted from the driving part 15, the calculating part 12 decides that the sensor 7 is inserted into the insertion hole 2. And, in accordance with the instruction from the calculating part 12, the driving part 15 allows the light source 4 to emit light.

The detecting part 14 is connected to the first light-receiving element 5 and the second light-receiving element 6. When signals are outputted from the light-receiving elements, the detecting part 14 outputs information for specifying the output values of the outputted signals to the calculating part 12. More specifically, the detecting part 14 subjects the output signals (analog signals) of the first light-receiving element 5 and the second light-receiving element 6 corresponding to the intensity of the received light to an A/D conversion so as to convert to digital signals, and outputs the digital signals to the calculating part 12.

The calculating part 12 calculates the absorbance of the target component (glucose) on the basis of the information stored in the memory part 13 and the information inputted from the detecting part 14, and further calculates the blood glucose level from the thus calculated absorbance. The calculating part 12 outputs the information for specifying the calculation result to the displaying part 16 so as to allow the displaying part 16 to display the calculation result.

Figure 2:
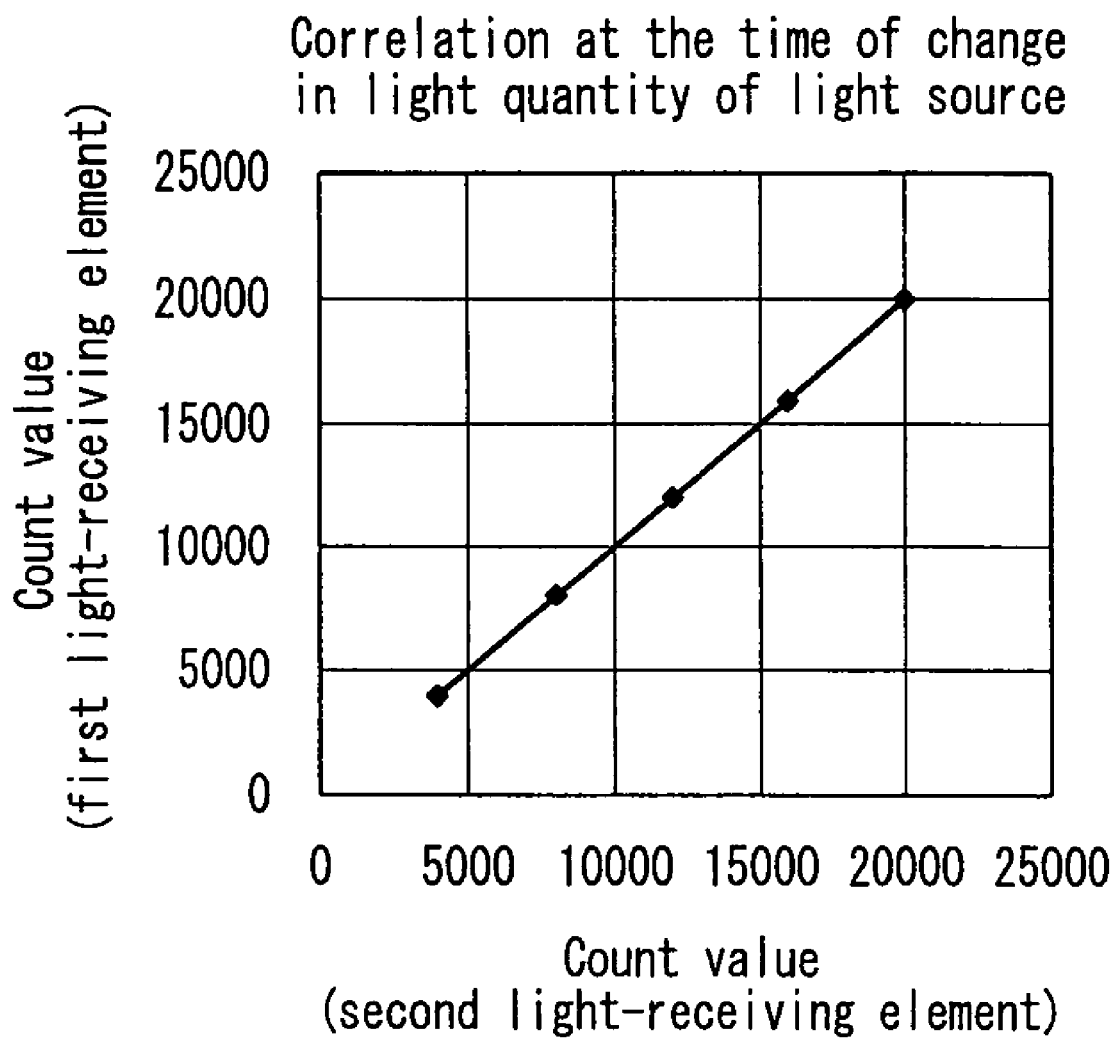
FIG. 2 is a graph showing a relationship between an output value of a first light-receiving element 5 and an output value of a second light-receiving element 6 when light is emitted from a light source 4 in a state where a sensor 7 is not inserted into an insertion hole 2 (where a sample is not present).

Next, procedures performed at the calculating part 12 in Example 1 and information stored in the memory part 13 will be specified below with reference to FIG. 2. FIG. 2 is a graph showing a relationship between the output value of the first light-receiving element 5 and the output value of the second light-receiving element 6 when light is emitted from the light source 4 in a state where the sensor 7 is not inserted into the insertion hole 2 (where a sample is not present).

In FIG. 2, the y-axis denotes a count value of the first light-receiving element 5 and the x-axis denotes a count value of the second light-receiving element 6. The count values of the first light-receiving element 5 and the second light-receiving element 6 are measured by varying the light quantity of the light source 4 from 100%, 80%, 60%, 40% to 20%. The count values are digital values obtained by subjecting the analog output signals (voltage values) of the light-receiving elements to an A/D conversion with a 16-bits A/D converter.

As shown in FIG. 2, the count value of the first light-receiving element 5 and the count value of the second light-receiving element 6 are in a proportional relationship with each other when light is radiated from the light source 4 in a state where the sensor 7 is not inserted into the insertion hole 2. Therefore, in a case where $A_{10}$ denotes the output value of the first light-receiving element 5 and $B_{10}$ denotes the output value of the second light-receiving element 6 when light is emitted from the light source 4 in a state where the sensor 7 is not inserted into the insertion hole 2, their correlation is expressed as a proportionality constant $t_1$ calculated from Formula (1) below. The proportionality constant $t_1$ is kept constant irrespective of the light quantity of the light source. The memory part 13 stores the proportionality constant $t_1$.

[Equation 9]

$$t_1 = A_{10}/B_{10} \qquad (1)$$

Here, $A_1$ and $B_1$ denote the output values of the first light-receiving element 5 and the second light-receiving element 6 respectively when the sensor 7 is inserted into the insertion hole 2 and light is radiated from the light source 4. $A_0$ denotes the output value of the first light-receiving element 5 when the sensor 7 is taken out from the insertion hole 2 and light is radiated from the light source 4 without modifying the light quantity setting of the light source 4. As the output value $A_0$ corresponds to the blank value explained in the paragraph of the Background Art, the absorbance S can be calculated from Formula (5) below.

[Equation 10]

$$S = \left(-\log \frac{A_1}{A_0}\right) \qquad (5)$$

Since the second light-receiving element 6 receives emitted light other than the transmitted light, the output value of the second light-receiving element 6 will not be influenced by the presence of the sensor 7 unless the light quantity setting of the light source 4 is modified. Therefore, even when the output value (blank value) of the first light-receiving element 5 is $A_0$, the output value of the second light-receiving element 6 will be $B_1$. As a result, Formula (6) below is established from FIG. 2 and the above Formula (1).

[Equation 11]

$$t_1 = A_0/B_1 \qquad (6)$$

When the above Formula (6) is transformed, it can be expressed as $A_0 = t_1 \cdot B_1$. This formula indicates that the blank value $A_0$ can be obtained from the proportionality constant $t_1$ and the output value $B_1$ of the second light-receiving element 6. Furthermore, by substituting this formula in the above Formula (5), Formula (2) below is established.

[Equation 12]

$$S = \left(-\log \frac{A_1}{B_1 \cdot t_1}\right) \qquad (2)$$

In the above Formula (2), $t_1$ value will not be changed by the variation in the light quantity of the light source 4. Furthermore, $(B_1 \cdot t_1)$ that corresponds to the blank value $A_0$ becomes a value in which the change in the light quantity of the light source 4 over time is taken into consideration, since the output value $B_1$ is measured every time that the light is emitted from the light source 4. That is, the absorbance S calculated by the calculating part 12 using the above Formula (2) is substantially as precise as the absorbance calculated by measuring the blank value at every measurement of the absorbance.

In view of these facts, the calculating part 12 can calculate accurately the absorbance S without measuring the blank value $A_0$, by previously calculating the proportionality constant $t_1$ from the Formula (1). The proportionality constant $t_1$ can be calculated, for example, by the calculating part 12 at the time of factory shipment of the measuring apparatus. In an alternative embodiment, the calculating part 12 calculates the proportionality constant $t_1$ at any arbitrary occasion selected by the user of the measuring apparatus.

Figure 3:
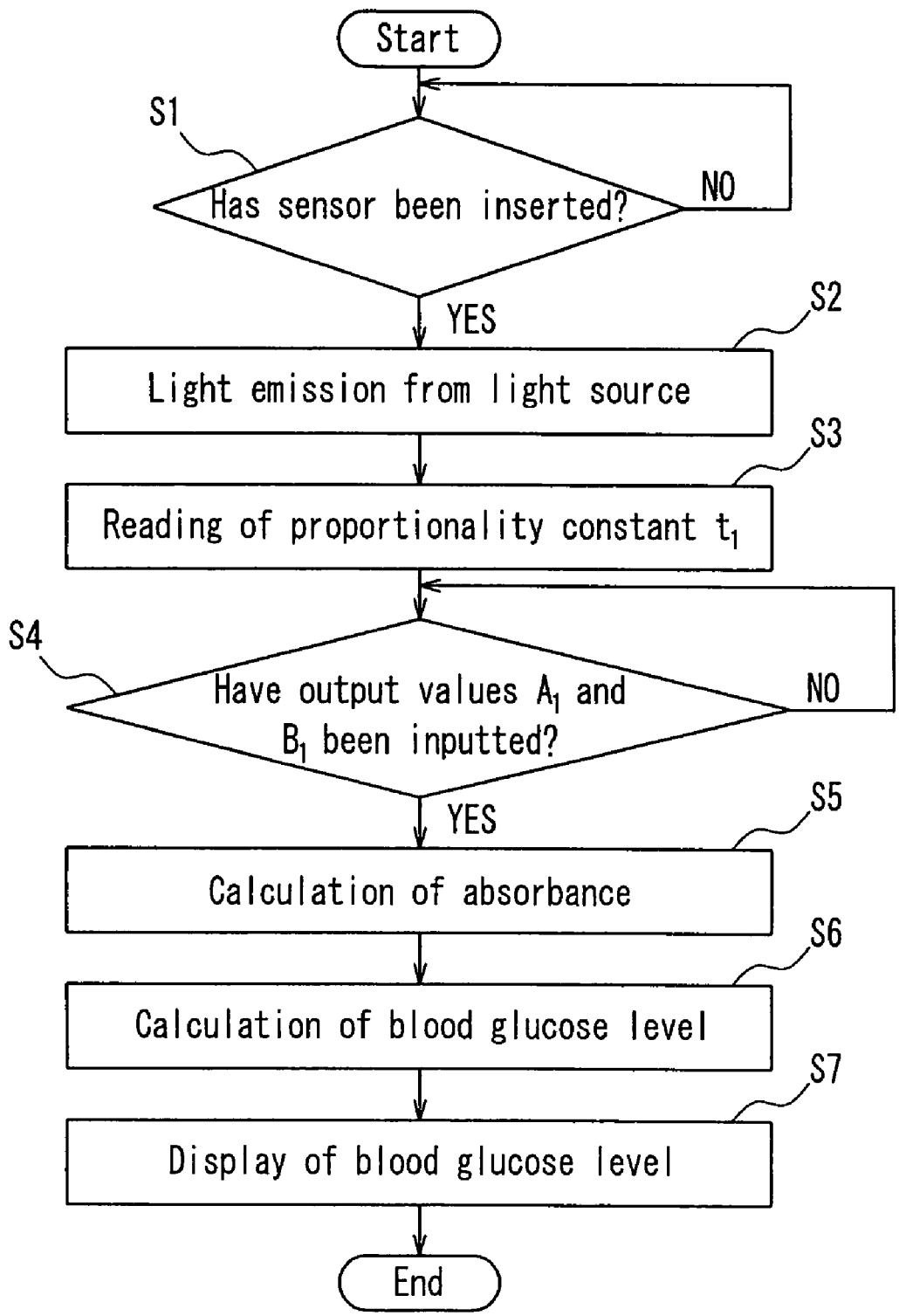
FIG. 3 is a flow chart showing operations of the measuring apparatus as shown in FIG. 1.

Next, the operations of the measuring apparatus in Example 1 will be described below with reference to FIG. 3. FIG. 3 is a flow chart showing operations of the measuring apparatus as shown in FIG. 1. As shown in FIG. 3, the calculating part 12 first decides via the driving part 15 whether or not the sensor 7 is inserted into the insertion hole 2 (step S1).

When the sensor 7 is not inserted into the insertion hole 2, that is, when a notification signal is not outputted from the driving part 15, the calculating part 12 enters the waiting state. When the sensor 7 is inserted into the insertion hole 2, that is, when a notification signal is outputted from the driving part 15, the calculating part 12 instructs the driving part 15 to allow the light source 4 to emit light (step S2). The driving part 15 notifies also to the calculating part 12 that the light source 4 emits light.

Next, the calculating part 12 reads out the proportionality constant $t_1$ from the memory part 13 (step S3). Furthermore, the calculating part 12 decides whether or not information that specifies the output value $A_1$ of the first light-receiving element and the output value $B_1$ of the second light-receiving element is inputted from the detecting part 14 (step S4). When the information is not inputted, the calculating part 12 enters the waiting state. When the information is inputted, the calculating part 12 calculates the absorbance S by using the above Formula (2) (step S5).

Furthermore, the calculating part 12 calculates the blood glucose level by using the absorbance S calculated in the step S5 (step S7). The blood glucose level can be obtained by storing previously a function expressing the relationship between the absorbance S and the blood glucose level in the memory part 13 and performing a calculation from the function. Alternatively, the blood glucose level can be calculated by storing in the memory part 13 the relationship between the absorbance S and the blood glucose level as "absorbance-blood-glucose-level table", and adapting a calculated absorbance S to this table.

Later, the calculating part 12 allows the displaying part 16 to display the calculated blood glucose level (step S7), thereby ending the procedure. When the sensor inserted into the insertion hole 2 is taken out and a new sensor 7 is inserted into the insertion hole 2, the calculating part 12 executes again the steps S1-S7. Similarly in this case, measurement of the blank value is not performed.

As mentioned above with reference to FIGS. 1-3, the measuring apparatus according to Example 1 can calculate a blank value necessary for calculating an absorbance, and thus, unlike conventional technology, there is no need to measure previously the blank value before measurement of the absorbance. Moreover, since the blank value obtained by the calculation is as accurate substantially as the blank value obtained by measurement, the calculated absorbance will be accurate as well. Furthermore, since there is no need to measure the blank value in the measuring apparatus according to Example 1, it is possible to suppress the tendency of complication in the operations, increase in the size of the apparatus, and the rise in cost for the apparatus.

Moreover, the measuring apparatus in Example 1 starts up only by insertion of the sensor 7 into the insertion hole 2 and immediately starts measurement of the absorbance, namely, the operability is excellent. Therefore, a user will not be forced to carry out any complicated operations or wait before an actual measurement. For example, the burdens on a diabetic patient can be decreased by applying the measuring apparatus according to Example 1 to a portable blood glucose meter that the patient uses several times a day.

In Example 1, the calculation unit 11 can be provided also by installing, in a microcomputer including an interface that can transmit and receive signals with external equipment, a program for performing the steps S1-S7 as shown in FIG. 3 and executing the program. In this case, the CPU (central processing unit) of the microcomputer functions as the calculating part 12, and a storing device such as a memory provided to the microcomputer functions as the memory part 13. The interface provided to the microcomputer functions as the detecting part 14 and also as the driving part 15.

Figure 4:
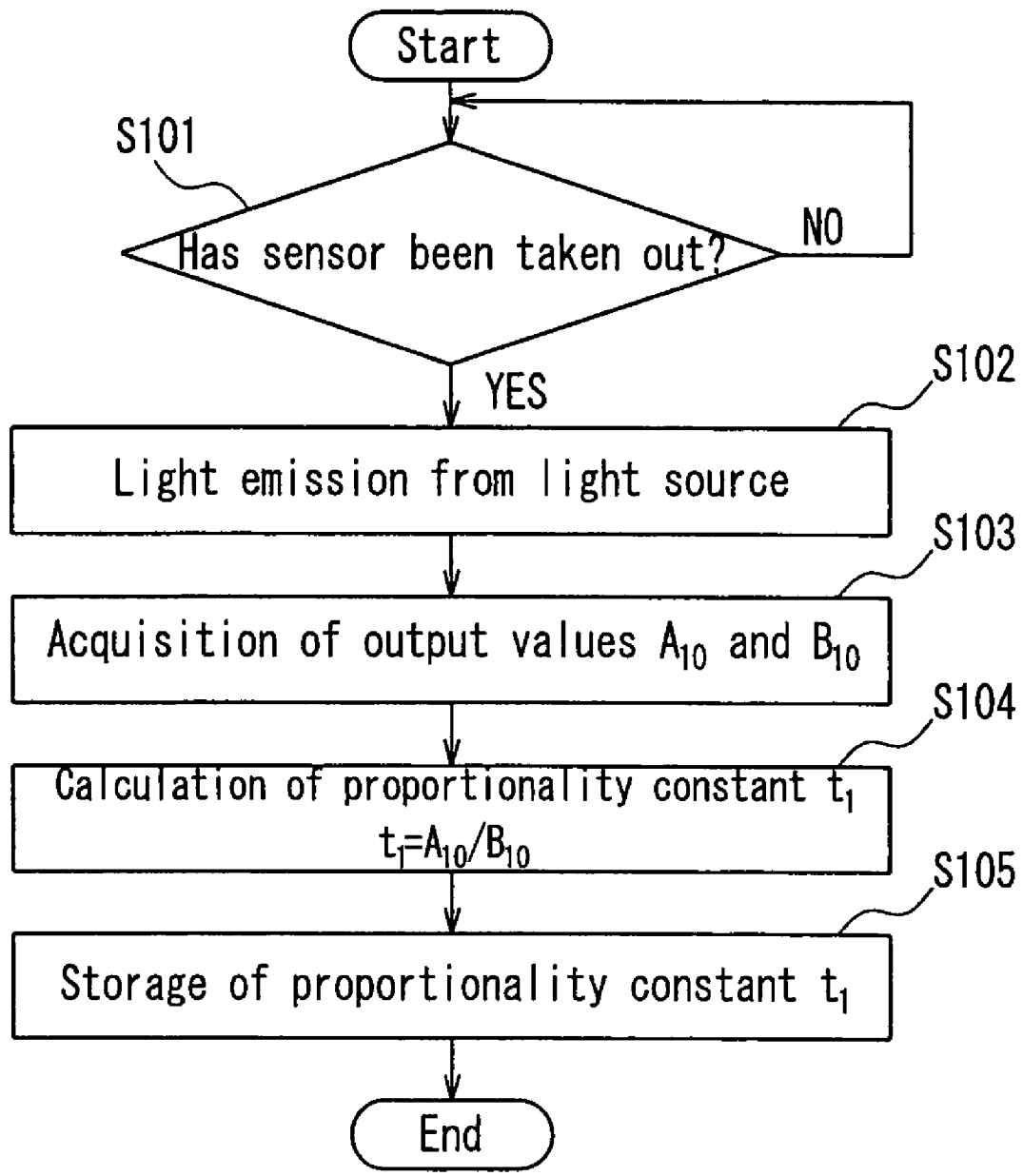
FIG. 4 is a flow chart showing a procedure of acquiring a proportionality constant performed by the measuring apparatus as shown in FIG. 1.

In Example 1, the measuring apparatus can perform a procedure of acquiring a proportionality constant $t_1$ to be used next time, after ending the steps S1-S7 as shown in FIG. 3. This will be explained below with reference to FIG. 4. FIG. 4 is a flow chart showing a procedure of acquiring the proportionality constant, which is performed by the measuring apparatus as shown in FIG. 1.

As shown in FIG. 4, the calculating part 12 decides first via the driving part 15 whether or not the sensor 7 has been taken out from the insertion hole 2 (step S101). Specifically, the calculating part 12 decides whether or not the output of the notification signal from the driving part 15 has been stopped. And when the output of the notification signal is stopped, the calculating part 12 decides that the sensor 7 has been taken out from the insertion hole 2.

When the sensor 7 is not taken out from the insertion hole 2, that is, when the output of the notification signal from the driving part 15 continues, the calculating part 12 enters the waiting state. When the sensor 7 is taken out from the insertion hole 2, that is, when the output of the notification signal from the driving part 15 is stopped, the calculating part 12 instructs the driving part 15 to allow the light source 4 to emit light (step S102).

Next, the calculating part 12 acquires the output value $A_{10}$ of the first light-receiving element and the output value $B_{10}$ of the second light-receiving element on the basis of the signal from the detecting part 14 (step S103). Subsequently, the calculating part 12 calculates the proportionality constant $t_1$ on the basis of the above Formula (1) (step S104), and stores the calculated proportionality constant $t_1$ in the memory part 13 (step S105), thereby ending the procedure. The proportionality constant $t_1$ calculated in the step S105 is read out in the step S3 for the next calculation of absorbance so as to be used for calculation of the absorbance.

As mentioned above, in an embodiment of executing a procedure of acquiring a proportionality constant $t_1$ to be used next time every time executing the steps S1 to S7 as shown in FIG. 3, errors that occur at the time of calculation of the absorbance can be reduced and thus a more accurate absorbance can be obtained. Moreover, even for a case of performing a procedure of acquiring a proportionality constant $t_1$ to be used next time, the user only needs to insert the sensor 7 into the insertion hole 2. Therefore, there is no need to carry out a complicated operation or wait before an actual measurement, and thus the operability will not be degraded.

Figure 5:
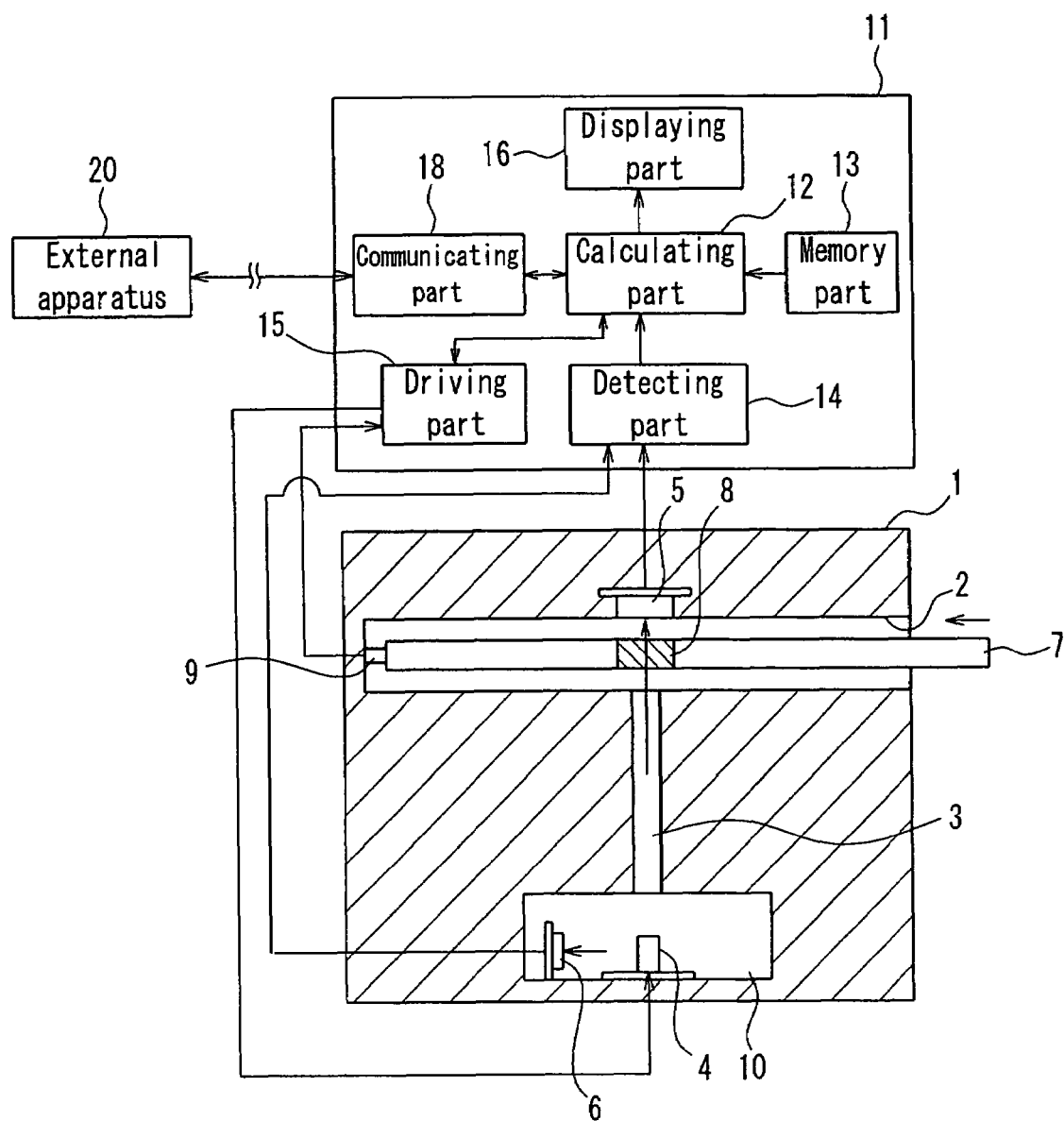
FIG. 5 is a schematic view showing an example of connection of an external unit to the measuring apparatus as shown in FIG. 1.

In a case of calculating the proportionality constant $t_1$ at the time of factory shipment of the measuring apparatus, an external apparatus 20 as shown in FIG. 5 can be used. FIG. 5 is a schematic view showing an example of connection of an external apparatus to the measuring apparatus as shown in FIG. 1. As shown in FIG. 5, in a case of connecting to the external apparatus 20, a communicating part 18 is provided further to the calculation unit 11. The communicating part 18 includes an interface circuit for transmitting/receiving signals to and from the external apparatus 20 by wire or wireless. The communicating part 18 can be attached temporarily to the measuring apparatus only for a case of connecting to the external apparatus 20.

The external apparatus 20 starts communications by wire or wireless with a completely assembled measuring apparatus, and instructs calculation of the proportionality constant $t_1$ and transmission of the calculated proportionality constant $t_1$. And when receiving the proportionality constant $t_1$ from the measuring apparatus, the external apparatus 20 transmits the proportionality constant $t_1$ to another measuring apparatus of the same type, and stores the proportionality constant $t_1$. This will be further specified below with reference to FIG. 6. For the explanation below, FIG. 5 will be referred to suitably.

Figure 6:
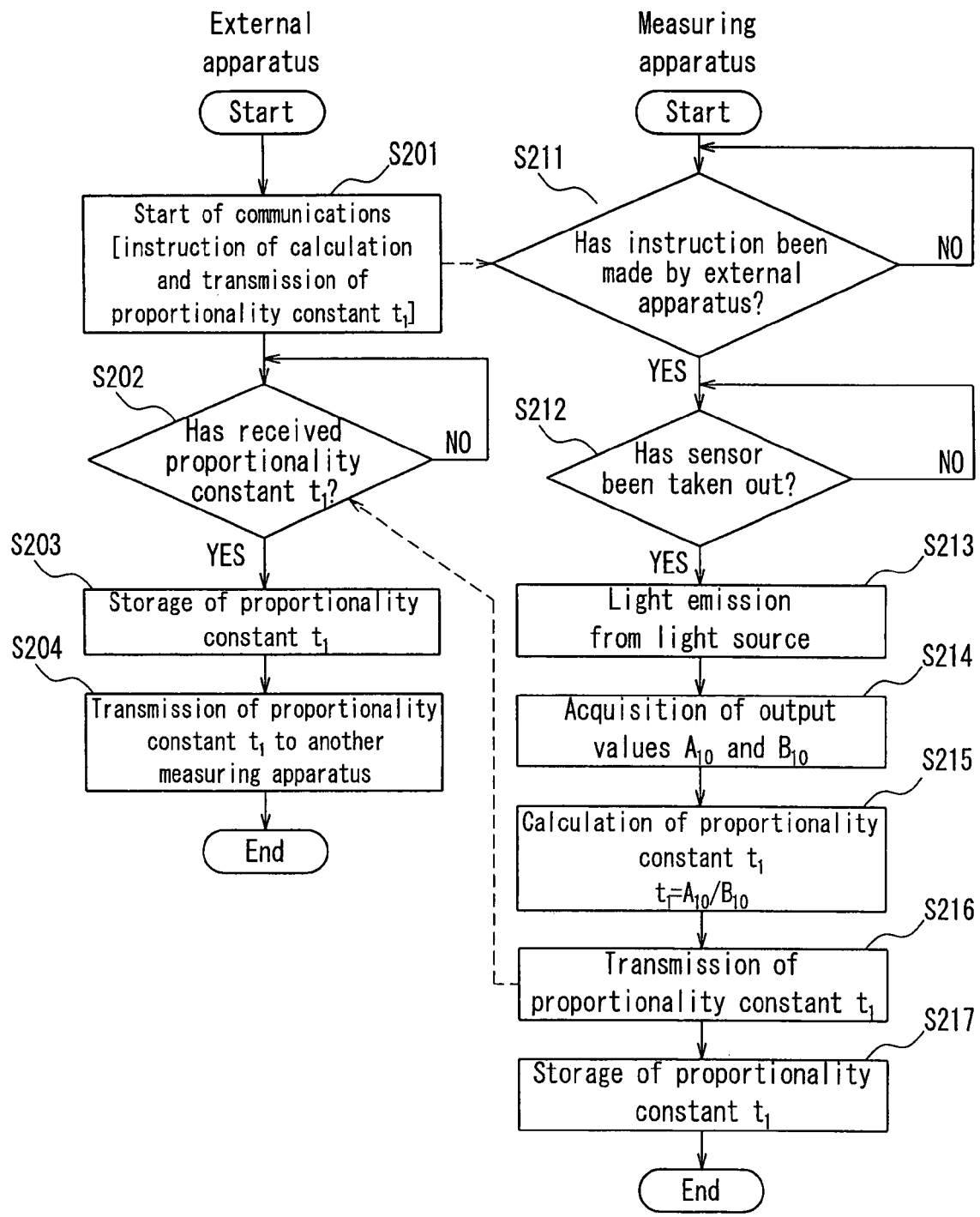
FIG. 6 is a flow chart showing a procedure in the external unit and the measuring apparatus as shown in FIG. 5.

FIG. 6 is a flow chart showing procedures in the external apparatus and the measuring apparatus as shown in FIG. 5. As shown in FIG. 6, the external apparatus 20 starts communications first with the completely assembled measuring apparatus so as to instruct calculation of the proportionality constant $t_1$ and transmission of the calculated proportionality constant $t_1$ (step S201).

In a measuring apparatus to be communicated with the external apparatus 20, the calculating part 12 decides first via the communicating part 18 whether or not there is an instruction of calculating and transmitting the proportionality constant $t_1$ by the external apparatus 20 (step S211). In a case where the instruction is not provided by the external apparatus 20, the calculating part 12 enters the waiting state.

In a case where instruction is provided by the external apparatus 20, the calculating part 12 executes the steps S212-S214 and then, calculates the proportionality constant $t_1$ (S215). The steps S212-S215 are the same steps as the steps S101-S104 shown in FIG. 4. Later, the calculating part 12 transmits the calculated proportionality constant $t_1$ to the external apparatus 20 via the communicating part 18 (step S216), and furthermore, stores the calculated proportionality constant $t_1$ in the memory part 13 (step S217), thereby ending the procedure.

After the step S201, the external apparatus 20 decides whether or not it has received the proportionality constant $t_1$ (step S202). In a case of a decision that the proportionality constant $t_1$ has not been received, the external apparatus 20 enters the waiting state. In a case where the proportionality constant $t_1$ has been received, the external apparatus 20 stores the received proportionality constant $t_1$ in its own memory part (memory) (step S203).

Later, the external apparatus 20 transmits the stored proportionality constant $t_1$ to another measuring apparatus of the same type (step S204), thereby ending the procedure. Alternatively, after ending the step S203, the external apparatus 20 can correct the proportionality constant $t_1$ in accordance with the ambient temperature or the like of the measuring apparatus. In a case where the correction is performed, the external apparatus 20 transmits the corrected proportionality constant $t_1$ to the measuring apparatus that has transmitted the proportionality constant $t_1$ or another measuring apparatus of the same type so as to store the corrected proportionality constant $t_1$.

In this manner, according to the example as shown in FIG. 5 and FIG. 6, it is possible to set a proportionality constant $t_1$ at a time with respect to a plurality of measuring apparatuses, the cost for producing the measuring apparatus can be decreased.

EXAMPLE 2

Figure 7:
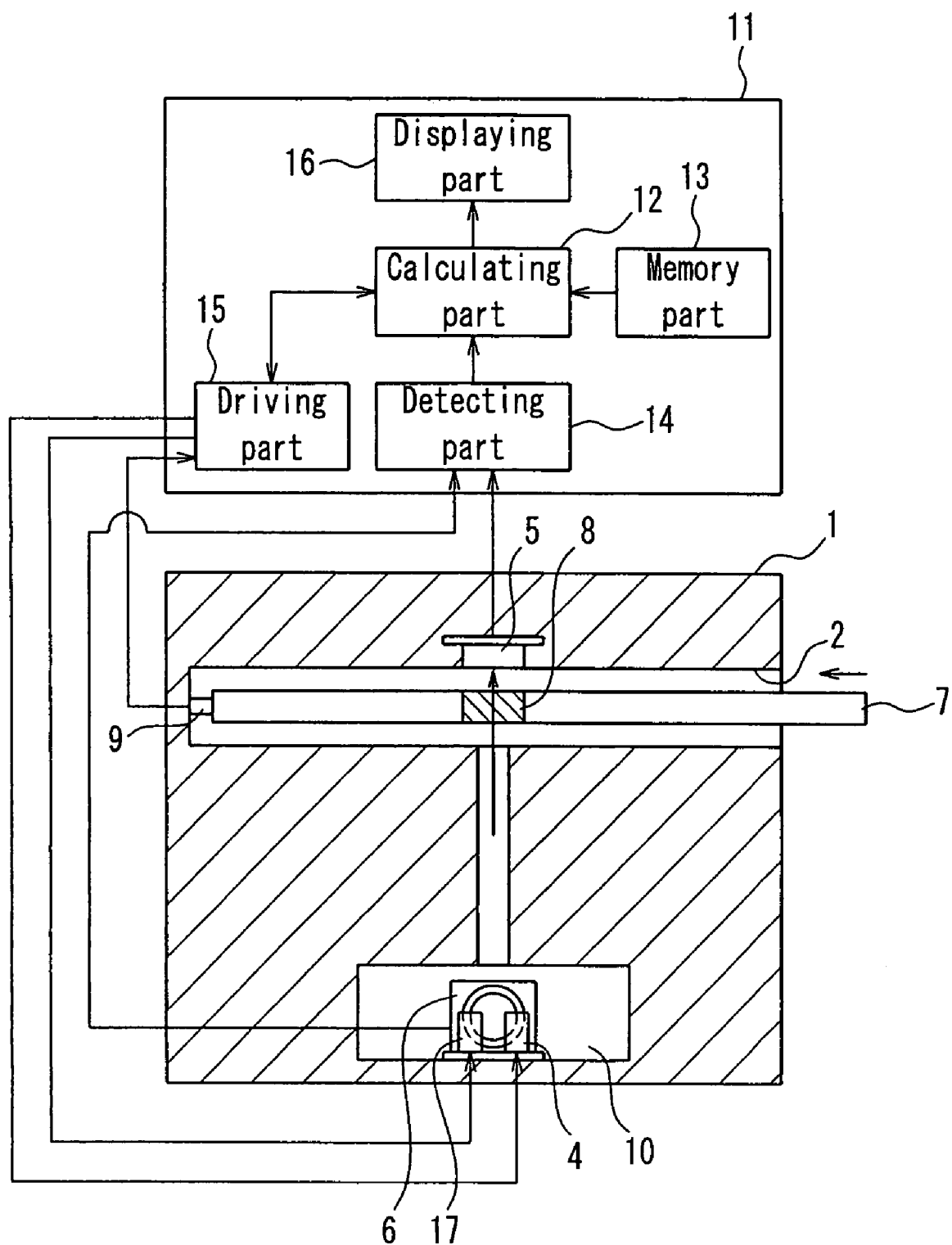
FIG. 7 is a schematic view showing a schematic configuration of a measuring apparatus according to Example 2 of the present invention.

Next, a measuring apparatus according to Example 2 of the present invention will be described with reference to FIGS. 7 and 8. First, the configuration of the measuring apparatus according to Example 2 will be described with reference to FIG. 7. FIG. 7 is a schematic view showing a schematic configuration of the measuring apparatus according to Example 2.

In Example 2, the measuring apparatus is used as a colorimetric blood glucose meter just as in Example 1. The sample is a patient's blood. Just like in Example 1, the component as a measurement target is the glucose that is included in the blood and develops color due to a reagent. However, unlike Example 1, the patient's blood used as the sample in this Example 2 is not centrifuged, and thus the blood sample contains blood cell components. In this case, since the light emitted from the light source 4 is absorbed partially by the blood cell components in the blood, calculation of accurate absorbance will be difficult with the measuring apparatus according to Example 1.

For the above-mentioned reason, as shown in FIG. 7, the measuring apparatus in Example 2 includes the light source 4 and also a second light source 17, unlike the measuring apparatus of the Example 1 as shown in FIG. 1. The wavelength of the light emitted from the second light source 17 is set to a wavelength not to be absorbed by glucose that develops color due to the reagent. The calculating part 12 performs a correction of the absorbance value by using the output values of the first light-receiving element 5 and the second light-receiving element 6 when the light is emitted from the second light source 17. Except for these matters, the measuring apparatus in Example 2 is configured similarly to the measuring apparatus in Example 1.

The following explanation is about the differences between the measuring apparatus in Example 2 and the measuring apparatus in Example 1. As shown in FIG. 7, the second light source 17 is arranged in parallel to the light source 4 so that the light emission direction will be the same as that of the light source 4. Therefore, transmitted light emitted from the second light source 17 and passed through the sample (sensor 7) (hereinafter, referred to as 'second transmitted light') also is received by the first light-receiving element 5.

According to Example 2, the second light-receiving element 6 is arranged so as to receive both light other than the transmitted light emitted from the first light source 4 and light other than the transmitted light emitted from the second light source 17. Specifically, the second light-receiving element 6 is arranged in the light source chamber 10, with its light-receiving plane facing both the first light source 4 and the second light source 17. There is no specific limitation on the distance between the second light-receiving element 6 and the first light source 4, the distance between the second light-receiving element 6 and the second light source 17, and the ratio of these distances, as long as there is no fluctuation.

In addition, according to the configuration, a graph similar to that in FIG. 2 can be obtained even when light is radiated from the second light source 17 in a state where the sensor 7 is not inserted into the insertion hole 2. Therefore, a correlation between $A_{20}$ and $B_{20}$ are expressed as a proportionality constant $t_2$ calculated from the following Formula (3), where $A_{20}$ and $B_{20}$ denote the output value of the first light-receiving element 5 and the output value of the second light-receiving element 6 respectively when light is emitted from the second light source 17 in a state where the sensor 7 is not inserted into the insertion hole 2.

[Equation 13]

$$t_2 = A_{20}/B_{20} \tag{3}$$

Similarly to the case of the proportionality constant $t_1$ as shown in the above Formula (1), the proportionality constant $t_2$ is kept constant irrespective of the light quantity of the light source. In Example 2, the memory part 13 stores the proportionality constant $t_2$ in addition to the proportionality constant $t_1$.

Here, $A_2$ and $B_2$ denote respectively the output values of the first light-receiving element 5 and the second light-receiving element 6 when the sensor is inserted into the insertion hole 2 and light is radiated from the second light source 17, and furthermore, S' denotes an absorbance at this time. Since the above Formula (3) is established, Formula (7) below can be derived similarly to the above Formula (2) as shown in Example 1.

[Equation 14]

$$S' = \left(-\log \frac{A_2}{B_2 \cdot t_2}\right) \tag{7}$$

As mentioned above, the wavelength of the light emitted from the second light source 17 is set to a wavelength not to be absorbed by glucose that develops color due to the reagent. Therefore, the absorbance S' calculated from the above Formula (7) corresponds to the absorbance of a blood cell component in the blood. Similarly to the case of the absorbance calculated from the above Formula (2), the absorbance S' is as precise as the absorbance calculated from a measurement of the blank value.

In Example 2, the blood as the sample contains blood cell components. Therefore, in a case where the calculating part 12 calculates the absorbance S of the target component by applying the above Formula (2) used in Example 1, the obtained absorbance value will be higher than the actual value since the light emitted from the light source 4 is absorbed partially by the blood cell component. Therefore, an accurate glucose absorbance can be obtained by subtracting the absorbance S' of the blood cell component from the absorbance obtained from the above Formula (2).

Namely, when the sample is a blood containing a blood cell component, an accurate absorbance S of the target component can be obtained by using the following Formula (4) that is derived from the above Formulas (2) and (7). In Example 2, the calculating part 12 calculates the absorbance S by using the Formula (4) below.

[Equation 15]

$$S = \left(-\log\frac{A_1}{B_1 \cdot t_1}\right) - \left(-\log\frac{A_2}{B_2 \cdot t_2}\right) \quad (4)$$

Similarly in Example 2, the proportionality constants $t_1$ and $t_2$ can be calculated by the calculating part 12 at a factory shipment of the measuring apparatus or at any arbitrary occasion selected by the user of the measuring apparatus.

Furthermore, when $t_1/t_2=t$, the above Formula (4) can be transformed to Formula (8) below. Therefore, in an alternative embodiment, the memory part 13 can store the constant t and the calculating part 12 can calculate the absorbance S by using the following Formula (8).

[Equation 16]

$$S = \left(-\log\frac{A_1}{A_2}\right) - \left(-\log\frac{B_1}{B_2} \cdot t\right) \quad (8)$$

Next, the operations of the measuring apparatus according to Example 2 will be explained with reference to FIG. 8. FIG. 8 is a flow chart showing operations of the measuring apparatus as shown in FIG. 7. As shown in FIG. 8, steps S11-S14 are executed first. The steps S11-S14 are the same as the steps S1-S4 as shown in FIG. 3 according to Example 1. As a result, the calculating part 12 reads out the proportionality constant $t_1$ from the memory part 13, and furthermore, on the basis of the input information from the detecting part 14, acquires the output value $A_1$ of the first light-receiving element 5 and the output value $B_1$ of the second light-receiving element 6 when light is emitted from the light source 4.

Next, the calculating part 12 instructs the driving part 15 to allow the second light source 17 to emit light (step S15). The driving part 15 notifies to the calculating part 12 that the second light source 17 emits light. Furthermore, the calculating part 12 reads out the proportionality constant $t_2$ from the memory part 13 (step S16).

Next, the calculating part 12 decides whether or not information for specifying the output value $A_2$ of the first light-receiving element 5 and the output value $B_2$ of the second light-receiving element 6 is inputted from the detecting part 14 (step S17). In a case where the information is not inputted, the calculating part 12 enters the waiting state. In a case where the information is inputted, the calculating part 12 calculates the absorbance S by using the above Formula (4) (step S18).

Later, the calculating part 12 calculates the blood glucose level (step S19) and allows the displaying part 16 to display the value (step S20), thereby ending the procedure. In a case where the sensor 7 in the insertion hole 2 is taken out and later a new sensor 7 is inserted into the insertion hole 2, the steps S11-S20 are executed again. In this case, similarly, measurement of the blank value is not performed.

As explained above with reference to FIGS. 7 and 8, the measuring apparatus in Example 2, similarly to Example 1, can obtain through a calculation the blank value necessary for the calculation of the absorbance. Therefore, unlike the conventional technique, there is no need to measure the blank value every time of measurement of absorbance.

The measuring apparatus according to Example 2 can measure the accurate absorbance of the target component even when the sample contains the target component and also a component that hinders transmission of light from the light source. Similarly in Example 2, the calculation unit 11 can be realized by a microcomputer.

Figure 9:
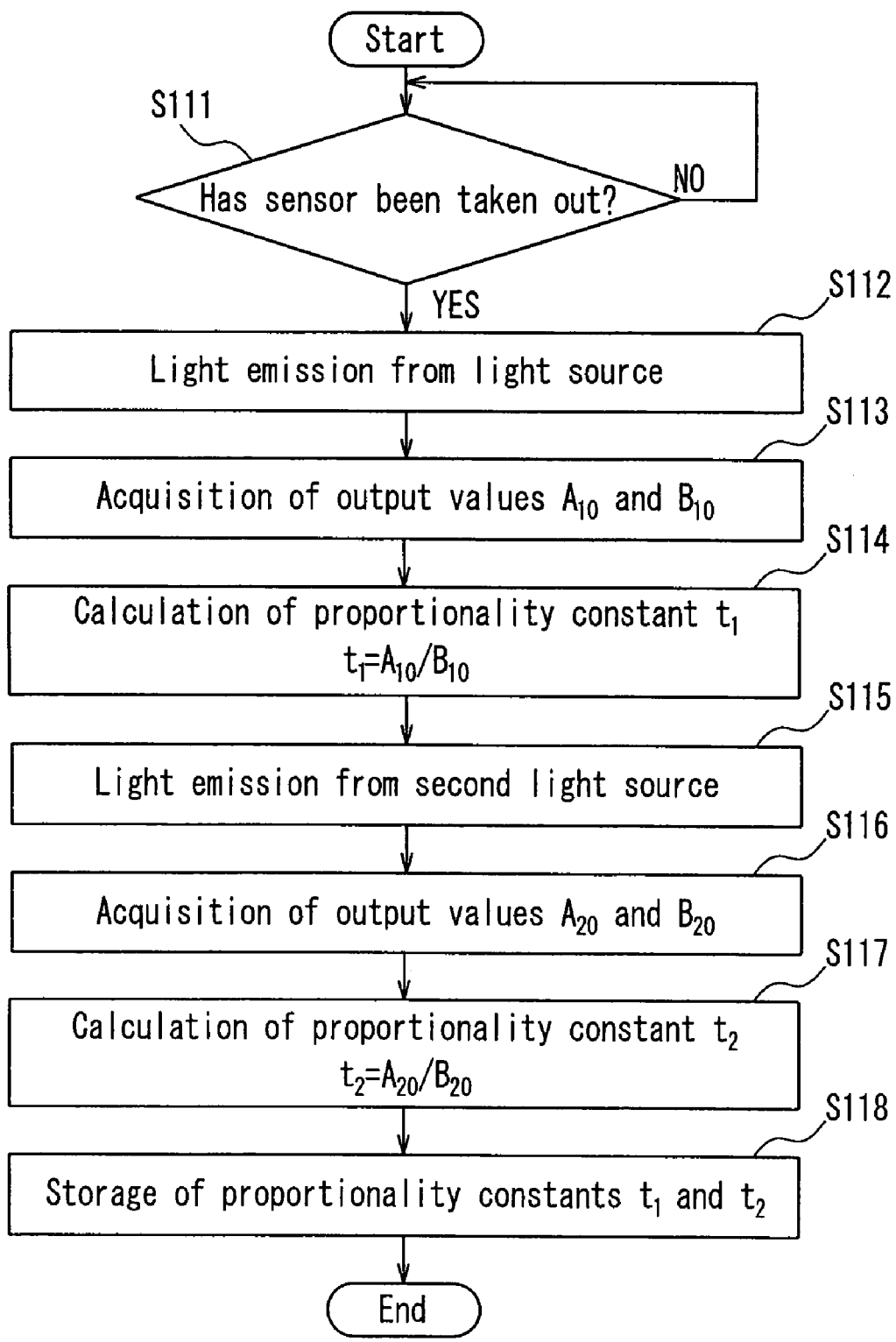
FIG. 9 is a flow chart showing a procedure of acquiring a proportionality constant performed by the measuring apparatus as shown in FIG. 7.

Similarly in Example 2, a procedure of acquiring the proportionality constants $t_1$ and $t_2$ to be used next time can be performed after ending the measurement by the measuring apparatus (after the step S11-S20). This will be explained with reference to FIG. 9. FIG. 9 is a flow chart showing the procedure of acquiring the proportionality constant performed by the measuring apparatus as shown in FIG. 7.

As shown in FIG. 9, the calculating part 12 executes steps S111-S114 first. The steps S111-S114 are the same step as the steps S101-S104 as shown in FIG. 4 according to Example 1. The proportionality constant $t_1$ is calculated by performing the steps S111-S114.

Next, the calculating part 12 instructs the driving part 15 to allow the second light source 17 to emit light (step S115). Subsequently, the calculating part 12 acquires the output value $A_{20}$ of the first light-receiving element 5 and the output value $B_{20}$ of the second light-receiving element 6 on the basis of the signal from the detecting part 14 (step S116). Subsequently, the calculating part 12 calculates the proportionality constant $t_2$ on the basis of the above-described Formula (3) (step S117). Later, the calculating part 12 stores in the memory part 13 the proportionality constant $t_1$ calculated in the step S114 and the proportionality constant $t_2$ calculated in the step S117 (step S118), thereby ending the procedure.

Figure 8:
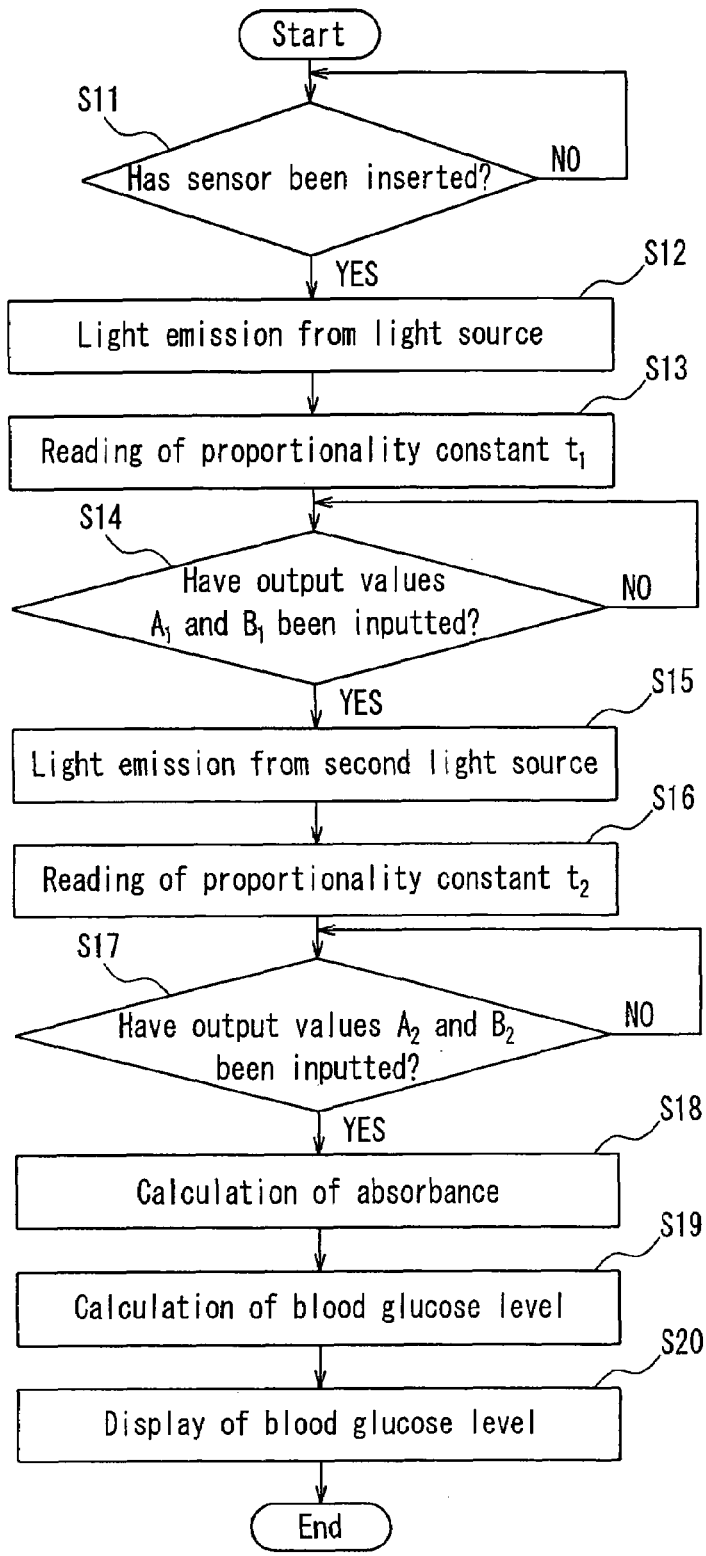
FIG. 8 is a flow chart showing operations of the measuring apparatus as shown in FIG. 7.

According to this embodiment where proportionality constants $t_1$ and $t_2$ to be used next time are acquired at every time of executing the steps S11-S20 as shown in FIG. 8, errors occurring at the time of calculation of the absorbance can be decreased, and thus more accurate absorbance can be obtained. Moreover, even when a procedure of acquiring the proportionality constants $t_1$ and $t_2$ to be used next time is performed, the user only has to insert the sensor 7 into the insertion hole 2. Therefore, there is no need to carry out any complicated operations or wait before the actual measurement, and thus the operability will not deteriorate.

Figure 10:
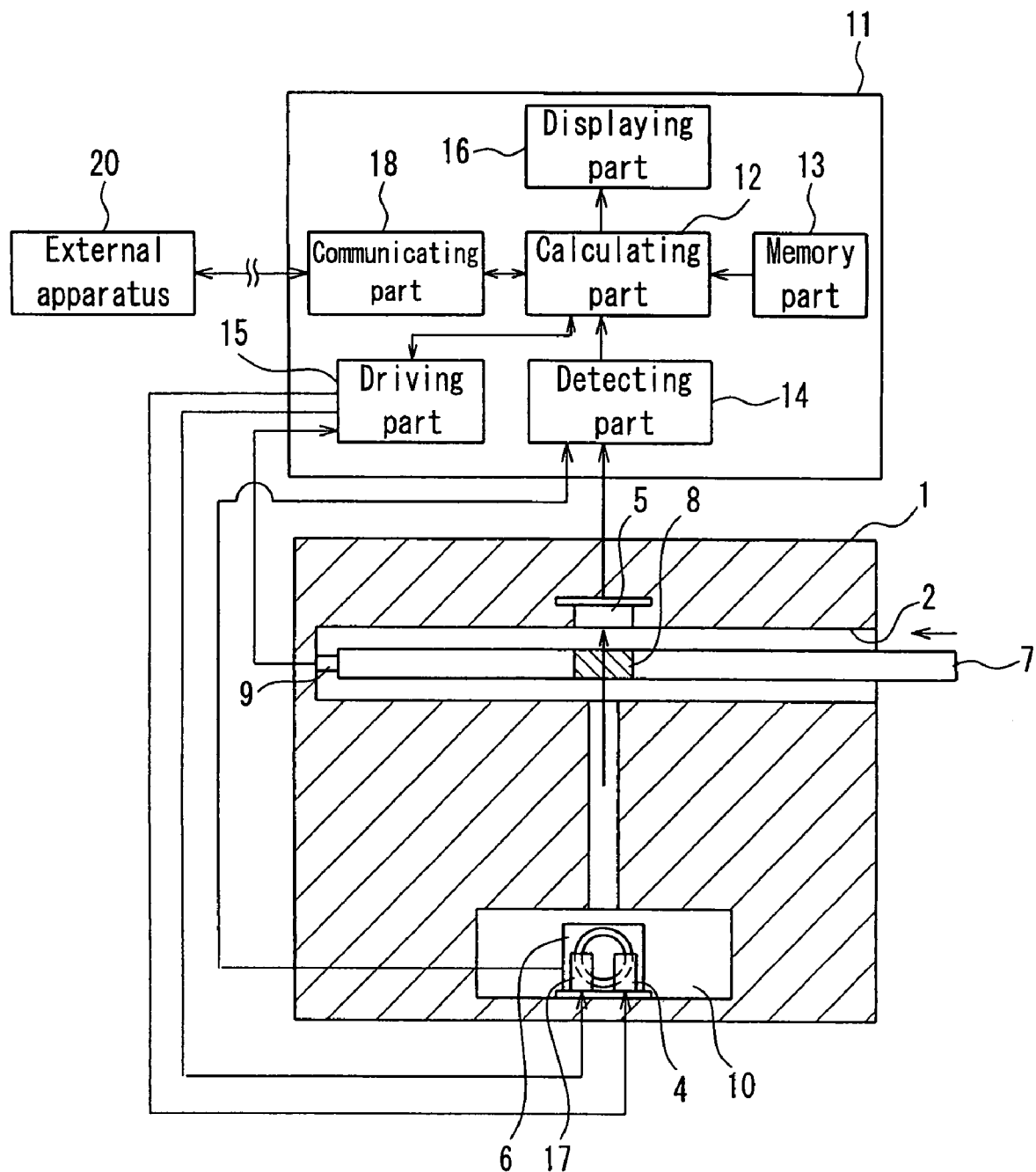
FIG. 10 is a schematic view showing an example of connection of an external unit to the measuring apparatus as shown in FIG. 7.

Similarly in Example 2, the external apparatus 20 as shown in FIG. 10 can be used in a case of calculating the proportionality constants $t_1$ and $t_2$ at a factory shipment. FIG. 10 is a schematic view showing an example where the external apparatus is connected to the measuring apparatus as shown in FIG. 7. As shown in FIG. 10, similarly in Example 2, a communicating part 18 is provided newly in the calculation unit 11 in a case of a connection to the external apparatus 20. Alternatively in Example 2, the communicating part 18 can be attached temporarily to the measuring apparatus only in a case of a connection to the external apparatus 20.

Similarly to Example 1, the external apparatus 20 starts communications by wire or wireless with the completely assembled measuring apparatus. In Example 2, the external apparatus 20 instructs calculation and transmission of not only the proportionality constant $t_1$ but also the proportionality constant $t_2$. Moreover, the external apparatus 20 transmits to another measuring apparatus of the same type not only the proportionality constant $t_1$ but also the proportionality constant $t_2$, and allows the storage. This will be explained more specifically with reference to FIG. 11. In the following explanation, FIG. 10 will be referred to suitably.

Figure 11:
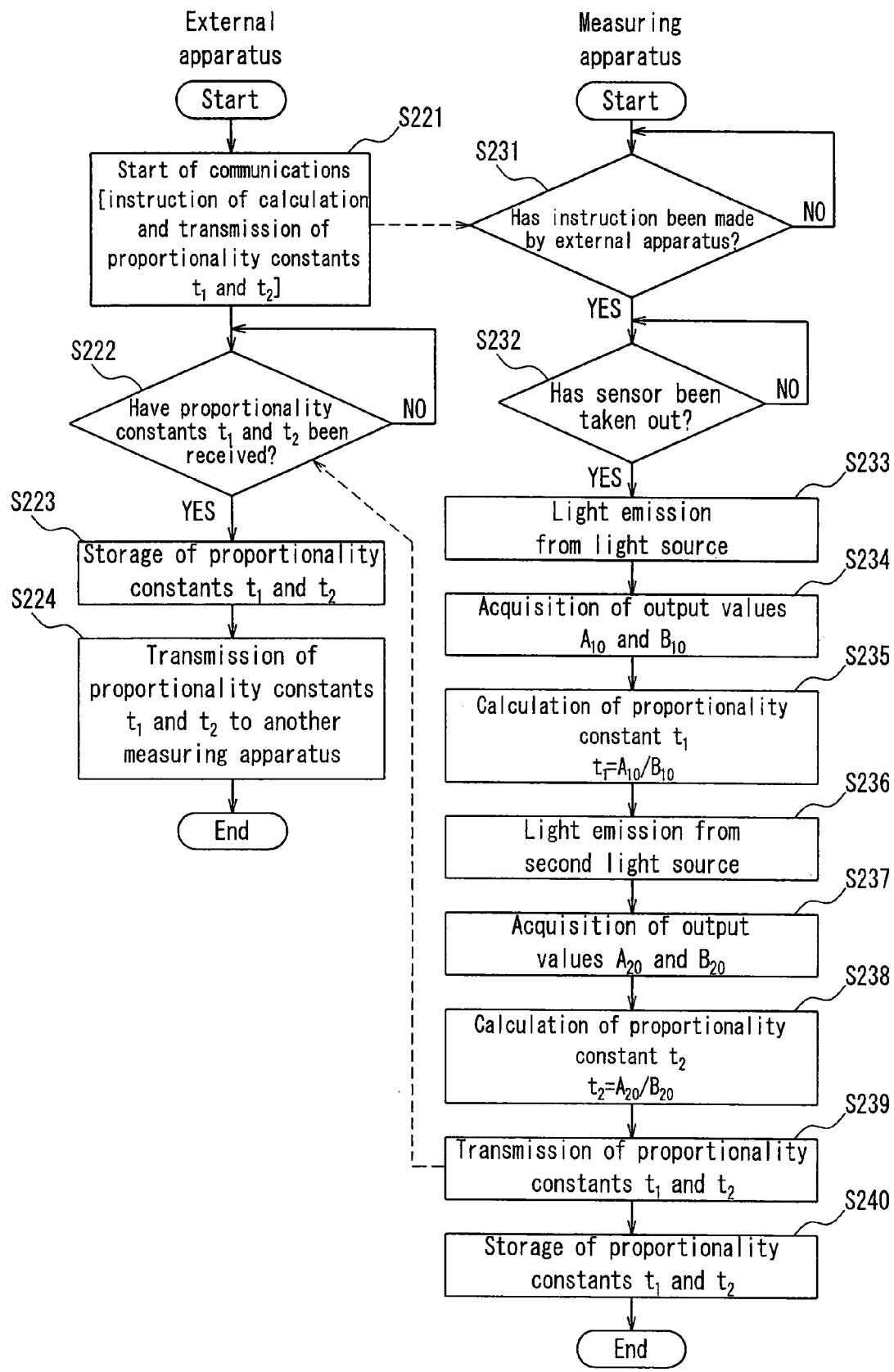
FIG. 11 is a flow chart showing procedures in the external unit and the measuring apparatus as shown in FIG. 10.

FIG. 11 is a flow chart showing procedures in the external apparatus and the measuring apparatus as shown in FIG. 10. As shown in FIG. 10, the external apparatus 20 first starts communications with the completely assembled measuring apparatus and instructs calculation of the proportionality constants $t_1$ and $t_2$ and transmission of the calculated proportionality constants $t_1$ and $t_2$ (step S221).

In a measuring apparatus to be communicated with the external apparatus 20, the calculating part 12 decides first via the communicating part 18 whether or not an instruction of calculation and transmission of the proportionality constants $t_1$ and $t_2$ is made by the external apparatus 20 (step S231). In a case where no instruction is made by the external apparatus 20, the calculating part 20 enters the waiting state.

In a case where an instruction is made by the external apparatus 20, the calculating part 12 executes steps S232-S235 so as to calculate the proportionality constants $t_1$, and further executes steps S236-S238 so as to calculate the proportionality constants $t_2$. The steps S232-S238 are the same as the steps S111-S117 as shown in FIG. 9.

Later, the calculating part 12 transmits the thus calculated proportionality constants $t_1$ and $t_2$ to the external apparatus 20 via the communicating part 18 (step S239), and furthermore, stores the thus calculated proportionality constants $t_1$ and $t_2$ in the memory part 13 (step S240), thereby ending the procedure.

After the step S221, the external apparatus 20 decides whether or not it has received the proportionality constants $t_1$ and $t_2$ (step S222). In a case where the external apparatus 20 has not received according to the decision, the external apparatus 20 enters the waiting state. When receiving, the external apparatus 20 stores the received proportionality constants $t_1$ and $t_2$ in its own memory part (memory) (step S223).

Later, the external apparatus 20 transmits the stored proportionality constants $t_1$ and $t_2$ to another measuring apparatus of the same type (step S224), thereby ending the procedure. Alternatively, in Example 2, after ending the step S223, the external apparatus 20 can correct the proportionality constants $t_1$ and $t_2$ in accordance with the ambient temperature or the like of the measuring apparatus. When such a correction is performed, the external apparatus 20 transmits the corrected proportionality constants $t_1$ and $t_2$ to the measuring apparatus that has transmitted the proportionality constants $t_1$ and $t_2$ or another measuring apparatus of the same type so as to allow the storage.

Accordingly, in Example 2, according to the example as shown in FIGS. 10 and 11, it is possible to set the proportionality constants $t_1$ and $t_2$ at a time with respect to a plurality of measuring apparatuses. Therefore, the cost for producing the measuring apparatus can be decreased.

INDUSTRIAL APPLICABILITY

As mentioned above, the measuring apparatus according to the present invention can measure the accurate absorbance without measuring the blank value, and thus the operations in the measuring apparatus can be simplified. As a result, when the measuring apparatus of the present invention is used for a portable blood glucose meter for a diabetic patient, burdens on the patient can be reduced.

The invention claimed is:

1. A measuring apparatus for measuring an absorbance of a target component contained in a sample, the measuring apparatus comprising:

a first light source for emitting light having a wavelength to be absorbed by the target component, a first light-receiving element and a second light-receiving element for outputting signals corresponding to the intensity of received light, a calculating part, and a memory part;

the first light-receiving element and the first light source are arranged so that transmitted light emitted from the first light source and passed through the sample is received by the first light-receiving element, the second light-receiving element is arranged to receive light other than the transmitted light emitted from the first light source, the memory part stores a correlation between an output value $A_{10}$ of the first light-receiving element and an output value $B_{10}$ the second light-receiving element when light is emitted from the first light source in a state where the sample is not present, wherein the sample contains a component to hinder an advance of light entering the sample;

the measuring apparatus further comprises a second light source for emitting light having a wavelength not to be absorbed by the target component;

the second light source is arranged so that second transmitted light emitted from the second light source and passed through the sample is received by the first light-receiving element, and that light other than the second transmitted light emitted from the second light source is received by the second light-receiving element, the memory part further stores a correlation between an output value $A_{20}$ of the first light-receiving element and an output value $B_{20}$ of the second light-receiving element when light is emitted from the second light source in a state where the sample is not present, the calculating part calculates the absorbance of the target component from an output value $A_1$ of the first light-receiving element and an output value $B_1$ of the second light-receiving element when light is emitted from the first light source in a state where the sample is present, an output value $A_2$ of the first light-receiving element and an output value $B_2$ of the second light-receiving element when light is emitted from the second light source in a state where the sample is present, the correlation between the output values $A_{10}$ and $B_{10}$ and the correlation between the output values $A_{20}$ and $B_{20}$.

2. The measuring apparatus according to claim 1, wherein the target component is glucose that is contained in the sample and develops color due to a reagent.

3. The measuring apparatus according to claim 1, wherein the sample is a blood that contains blood cell components, and the target component is glucose that is contained in the blood and develops color due to a reagent.

4. The measuring apparatus according to claim 1, wherein the correlation between the output values $A_{10}$ and $B_{10}$ is expressed as a proportionality constant $t_1$ calculated by Formula (1) below;

the correlation between the output values $A_{20}$ and $B_{20}$ is expressed as a proportionality constant $t_2$ calculated by Formula (2) below; and the calculating part calculates the absorbance of the target component S on the basis of Formula (3) below:

[Formula 1]

$$t_1 = A_{10}/B_{10} \qquad (1)$$

[Formula 2]

$$t_2 = A_{20}/B_{20} \qquad (2)$$

[Formula 3]

$$S = \left(-\log\frac{A_1}{B_1 \cdot t_1}\right) - \left(-\log\frac{A_2}{B_2 \cdot t_2}\right). \quad (3)$$

5. The measuring apparatus according to claim 4, wherein when the sample is not present, the calculating part allows the first light source to emit light so as to acquire the output value $A_{10}$ of the first light-receiving element and the output value $B_{10}$ of the second light-receiving element, substitutes in Formula (1) the acquired output value $A_{10}$ of the first light-receiving element and the output value $B_{10}$ of the second light-receiving element so as to calculate the proportionality constant $t_1$, stores the calculated proportionality constant $t_1$ in the memory part, and calculates the absorbance S of the target component by using the stored proportionality constant $t_1$.

6. The measuring apparatus according to claim 4, wherein when the sample is not present, the calculating part allows the second light source to emit light so as to acquire the output value $A_{20}$ of the first light-receiving element and the output value $B_{20}$ of the second light-receiving element, substitutes in Formula (2) the acquired output value $A_{20}$ of the first light-receiving element and the output value $B_{20}$ of the second light-receiving element so as to calculate the proportionality constant $t_2$, stores the calculated proportionality constant $t_2$ in the memory part, and calculates the absorbance S of the target component by using the stored proportionality constant $t_2$.

* * * * *